(12) United States Patent
Rohlf et al.

(10) Patent No.: US 9,518,363 B2
(45) Date of Patent: Dec. 13, 2016

(54) ANTIMICROBIAL SIZE EMULSION AND GYPSUM PANEL MADE THEREWITH

(71) Applicant: United States Gypsum Company, Chicago, IL (US)

(72) Inventors: Evan V. Rohlf, Tower Lakes, IL (US); Mark B. Scalf, McHenry, IL (US)

(73) Assignee: UNITED STATES GYPSUM COMPANY, Chicago, IL (US)

( * ) Notice: Subject to any disclaimer, the term of this patent is extended or adjusted under 35 U.S.C. 154(b) by 348 days.

(21) Appl. No.: 14/257,411

(22) Filed: Apr. 21, 2014

(65) Prior Publication Data

US 2014/0227545 A1  Aug. 14, 2014

Related U.S. Application Data

(62) Division of application No. 13/287,185, filed on Nov. 2, 2011, now Pat. No. 8,747,534.

(60) Provisional application No. 61/428,080, filed on Dec. 29, 2010.

(51) Int. Cl.
| | |
|---|---|
| *D21H 21/36* | (2006.01) |
| *D21H 17/07* | (2006.01) |
| *D21H 21/16* | (2006.01) |
| *A01N 33/12* | (2006.01) |
| *E04C 2/04* | (2006.01) |

(52) U.S. Cl.
CPC .............. *D21H 21/36* (2013.01); *A01N 33/12* (2013.01); *D21H 17/07* (2013.01); *D21H 21/16* (2013.01); *E04C 2/043* (2013.01); *Y10T 428/31993* (2015.04); *Y10T 428/31996* (2015.04)

(58) Field of Classification Search
None
See application file for complete search history.

(56) References Cited

U.S. PATENT DOCUMENTS

| | | |
|---|---|---|
| 3,435,039 A | 3/1969 | Wakeman et al. |
| 3,524,796 A | 8/1970 | Yui et al. |
| 4,088,600 A | 5/1978 | Tutein et al. |
| 4,107,060 A | 8/1978 | Schick et al. |
| 4,522,686 A | 6/1985 | Dumas |
| 4,606,773 A | 8/1986 | Novak |
| 4,719,029 A | 1/1988 | Hardy |
| 5,049,383 A | 9/1991 | Huth et al. |
| 5,082,697 A | 1/1992 | Patton et al. |
| 5,084,096 A | 1/1992 | Stovicek |
| 6,159,339 A | 12/2000 | Hassler et al. |
| 6,342,466 B1 | 1/2002 | Dookhith et al. |
| 6,409,823 B1 | 6/2002 | Shake et al. |
| 6,489,040 B1 | 12/2002 | Rohlf et al. |
| 6,680,127 B2 | 1/2004 | Capps |
| 6,893,752 B2 | 5/2005 | Veeramasuneni et al. |
| 7,309,516 B2 | 12/2007 | Nelson et al. |
| 7,473,474 B2 | 1/2009 | Toreki et al. |
| 2004/0238138 A1 | 12/2004 | Ishizaki et al. |
| 2005/0250888 A1 | 11/2005 | Lettkeman et al. |
| 2006/0194072 A1 | 8/2006 | Toreki et al. |
| 2006/0254738 A1* | 11/2006 | Anderson ............... C08L 3/04 162/175 |
| 2007/0048346 A1 | 3/2007 | Ido |
| 2007/0149694 A1 | 6/2007 | Krishnan |
| 2007/0151685 A1 | 7/2007 | Horsfield et al. |
| 2008/0194532 A1 | 8/2008 | Rabinovich-Guilatt et al. |
| 2010/0056479 A1 | 3/2010 | Sauer et al. |
| 2010/0105768 A1 | 4/2010 | Jiang et al. |
| 2010/0126383 A1 | 5/2010 | Berkemans et al. |

FOREIGN PATENT DOCUMENTS

| | | |
|---|---|---|
| FR | 2 281 335 | 3/1976 |
| JP | 2009-242686 | 10/2009 |
| WO | WO 99/55505 | 11/1999 |
| WO | WO 03/051114 | 6/2003 |
| WO | WO 2004/038120 | 5/2004 |
| WO | WO 2008/027430 | 3/2008 |
| WO | WO 2008/049616 | 5/2008 |
| WO | WO 2008/091794 | 7/2008 |
| WO | WO 2008/145146 | 12/2008 |

\* cited by examiner

*Primary Examiner* — Sheeba Ahmed
(74) *Attorney, Agent, or Firm* — Greer, Burns & Crain, Ltd.; Pradip Sahu; Philip T. Petti

(57) ABSTRACT

Disclosed is an emulsion of an internal paper size and a biocidal emulsifying agent, such as a cationic non-starchy quaternary ammonium compounds, that is introduced into a paper-making furnish to produce an anti-microbial paper. The antimicrobial paper is useful as facing for gypsum panels. A method of making the paper includes emulsifying the internal size with a biocide before introducing the size to the paper furnish. A method of making a microbial growth resistant gypsum panel that incorporates the antimicrobial paper is also disclosed.

8 Claims, No Drawings

ANTIMICROBIAL SIZE EMULSION AND GYPSUM PANEL MADE THEREWITH

RELATED APPLICATION

This application is a divisional application of U.S. patent application Ser. No. 13/287,185 filed Nov. 2, 2011 and which claims priority pursuant to 35 U.S.C. 119(e) from U.S. Provisional Application Serial No. 61/428,080 filed Dec. 29, 2010.

FIELD OF THE INVENTION

This invention relates to an emulsion of an alkenylsuccinic anhydride paper size ("ASA") or an alkyl ketene dimer ("AKD") paper size and a biocide whereby the biocide has a dual function as a biocide and an emulsifying agent.

BACKGROUND

Gypsum boards, also known as gypsum panels, drywall and wallboards, are popular construction materials with desirable properties for indoor applications. They are durable, economical and fire-retardant. In addition, these boards provide excellent compressive strength properties and a relatively low density. They are easily decorated and are attractive as surfaces, especially for interior construction.

Manufacturing of gypsum boards includes forming a slurry of calcium sulfate hemihydrate, water and additives and continuously depositing the slurry on a conveyor belt or a forming table. Often, a paper cover sheet, also known as a facer, moves on the conveyor beneath a mixer to continuously deposit slurry on the facer. Often, a second paper cover sheet, or facer, is applied over the slurry. The resultant assembly is formed into the shape of a panel. Calcium sulfate hemihydrate reacts with water in the slurry, converting the hemihydrate into a matrix of interlocking calcium sulfate dihydrate crystals, causing the slurry to set and become firm. This forms a continuous strip of hardened material having, optionally, no cover sheets, a front and back cover sheet, or just one cover sheet on either the front or back of the panel. The continuous strip moves on the conveyor until the calcined gypsum is sufficiently set to withstand handling and movement from the conveyor to another place, such as a kiln, and the strip is thereafter cut to form boards of desired length. Water that is in excess of the amount needed for hydration of the calcined gypsum is removed from the gypsum panel in a kiln.

Gypsum panel manufacturers often use a biocide to protect the panels from attack by microorganisms such as mold and fungi by treating the paper coverings. However, treated paper alone is often insufficient to control mold growth for a number of reasons. Many biocides lose efficacy through the drying process in the kiln due to the high temperatures. The biocide can be overwhelmed by large quantities of mold spores that are incorporated into the gypsum and paper from water used during the panel forming process, combined with spores from the air. In some cases, per environmental regulations, there is a limit to the concentration of biocide that can be present on the surface of the paper. It appears that the maximum allowable biocide concentration is not sufficient to protect both the paper and the set gypsum core in all cases.

Microbial growth favors environments where spores find moisture and nutrients to metabolize. Temperature is also a factor, but numerous species of microorganisms thrive at the temperatures required for human habitation, where gypsum boards are most often used. Therefore, opportunities to control microbial growth consist mostly of controlling availability of moisture and nutrients. It is desirable to have a mechanism for killing microorganisms that begin to grow in or on a gypsum panel or a facer. Water vapor and spores are unavoidable in environments where gypsum panels are used, even though gypsum board is normally used in interior construction. In addition to moisture that is present in the environment, products used in interior construction sometimes encounter water due to seepage, leaky roofs or pipes, flooding, condensation, and the like. These exposures occur without any defects in the gypsum board manufacture or use. It is accepted that once exposed to moisture, traditional gypsum panel products are susceptible to microbial growth.

Starch is an example of a nutrient that microorganisms thrive on. In gypsum panels, starch is frequently used for a number of purposes. It may be added to a calcined gypsum slurry to promote adhesion between the core and the facer. Often a facer is made of paper, and starch may be a component of the paper commonly used to cover gypsum panels. Starch (sugar) coated particles of calcium sulfate dihydrate are often used as a set accelerator in a calcined gypsum slurry. Other starches may also be used to modify different properties of the set gypsum composition. When starches are present in the cover materials or the gypsum cores of gypsum panels, there is sufficient nutrition for possible microbial growth once the spores come into contact with the nutritious medium of the farinaceous panel.

Cover sheets for gypsum panels, also known as facers, facing material, paper facers, etc., are made by a paper manufacturing processes that begins with preparation of a dilute pulp of fibers, chemical additives and water. The pulp is drained through a screen to form a mat of randomly intertwined fibers. Additional water is removed by pressing the mat or applying suction. Informally, the "wet end" refers to the paper-making process before water removal, and the stage of the process after excess water is removed is called the "dry end." Additives, such as size, may be added during either or both of these stages.

Paper size is a hydrophobic compound that improves a paper's strength and its resistance to penetration by liquids such as water and ink. Alkyl ketene dimer ("AKD") and alkenylsuccinic anhydride ("ASA"), both of which are hydrophobic, are common sizing agents. Rosin and rosin derivatives are another class of paper sizing agents known in the paper industry. For good sizing efficiency, the size is applied as very small particles. This, and the hydrophobic property, requires that ASA and/or AKD be emulsified in an aqueous solution in order to properly introduce and anchor the sizing to the paper's fibers. Internal size is incorporated into the paper itself during the wet end of the manufacturing process. External size is applied to the surface of the finished paper product by dry end coating processes such as dipping, spraying or rolling.

ASA internal size is usually prepared on-site at a paper plant by emulsion with a cationic starch stabilizer as described in U.S. Pat. No. 6,159,339, herein incorporated by reference. A high charge, low molecular weight polymer may also be used as an emulsifier of the internal paper size in water. Alternatively, an AKD emulsion may be prepared by first dispersing a starch phosphate derivative in the water which is to become the continuous phase of the emulsion. Then, AKD is added and thoroughly admixed at temperatures from about 140° F.-160° F. until a smooth, homogeneous emulsion is attained. High shear mixing equipment is used to agitate the ketene dimmer and aqueous starch phosphate mixture to attain the desired emulsion.

Disadvantages associated with known AKD emulsification practices are typically overcome by emulsifying the AKD off-site and supplying it to paper manufacturers as a fully formulated emulsion. Emulsifying AKD is a difficult process that ordinarily requires expensive and highly specialized equipment. For the purpose of stabilizing AKD emulsions, additives such as surfactants and protective colloids may be present in the emulsion composition. The AKD may react with some of these additives, thereby reducing the efficiency of the size by reducing the amount of active ingredient that is available. Anionic surfactants present in an AKD emulsion further reduce efficiency of the size because the cellulosic material to which the size is expected to anchor is also anionic, thereby repelling the size particles rather than favoring introduction of the size to the cellulosic fibers. Another disadvantage of the typical AKD emulsion supply is economic because it is expensive to transport the large amounts of water that are part of the AKD emulsion to the paper manufacturer.

ASA emulsions are unstable, with a maximum shelf life between 6 and 8 hours depending on the make down water pH and temperature. Typically, the ASA emulsion is stored for 30 minutes prior to use. It is desirable to keep the ASA oil very dry and to wait until the last possible moment to prepare the aqueous emulsion. Frequently, paper-makers prepare the desired amount of ASA emulsion 30 minutes before the solution is added to the furnish. Cationic starch emulsifiers utilized in preparation of the aqueous ASA size emulsions provide a cationic starch sheath around each ASA droplet, anchoring the size to the anionic cellulosic paper fibers. It is still possible for much of the ASA to flow from the fibers with the process water. This gives the ASA time to decompose by hydrolysis, impairing the ASA sizing efficiency, causing deposit to form on the paper machine, higher operating costs and paper quality issues. Complicated and expensive wet end chemistry is often needed to achieve satisfactory retention of the size. Dry end testing, such as high performance liquid chromatography ("HPLC") is common to ensure that retention of the ASA size is satisfactory and that it is consistent.

Prior art attempts to reduce microbial growth on gypsum boards include replacing paper facings with fiberglass-based facings, eliminating a source of starch nutrition and deterring microorganisms from growing on the board surfaces. Attempts to make gypsum boards resistant to microbial growth have also been made by incorporation of a biocide, such as a salt of pyrithione, into the core, the facers, or both, as revealed in U.S. Pat. No. 6,893,752 entitled "Mold Resistant Gypsum Panel and Method of Making Same," herein incorporated by reference.

Quaternary ammonium compounds are loosely defined as a class of compounds generally having the formula $R_1R_2R_3R_4$—$N^+Y^-$, where the radicals may be the same, different or part of a ring and Y is a counter anion. Typically, but not always, one of the radicals is a long-chain alkyl group. Certain quaternary ammonium compounds possess biocidal properties. Prior art teaches the use of biocidal quaternary ammonium compounds in the gypsum core, or as a surface coating of paper facers, whether applied by spraying, dipping, rolling or any other dry end coating method.

While quaternary ammonium compounds are appreciated for their ability to control the growth of microorganisms, they are often avoided in paper-making because they produce foam, even at low concentrations. Foam has detrimental effects on the quality of the final paper product by forming pin-holes, circular marks on the paper, lower paper strength and reduced production. Often, the solution to foam problems involves complicated wet end chemistry to prevent foam formation with anti-foam compounds or to de-foam the paper furnish with de-foaming compounds. Another method of controlling foam in aqueous solutions of quaternary ammonium compounds is by adding anionic surfactants to the solution, as disclosed in International Publication Number WO 2008/049616 entitled "Controlled Foam Aqueous Quaternary Ammonium And Phosphonium Compositions," herein incorporated by reference. As noted in this publication, the biocidal efficacy of quaternary ammonium compounds is compromised by addition of the anionic surfactant.

There is an ongoing need for gypsum board products that offer reduced susceptibility to microbial growth without compromising their beneficial properties. In addition, there is an ongoing need for commercially viable manufacturing methods for such products. There also remains a need for improvement in the efficiency and workability of AKD and ASA paper size as well as an improvement in retention of biocide compounds used in paper-making.

SUMMARY

One or more of these needs is met by the present invention, which features a biocidal sizing emulsion of a size and a biocidal emulsifying agent in water. The biocidal sizing emulsion is used to make a biocidal paper for use on a gypsum panel. Yet another embodiment is a biocidal gypsum panel with a paper facer that includes the biocidal sizing emulsion.

Surprisingly, the paper with beneficial properties provided by both a size and a biocide can be made without separate emulsifying agents and biocidal compounds. Biocidal emulsifying agents have been found, unexpectedly, to emulsify an internal paper size for addition to a furnish of a paper-making manufacturing process. Efficiencies and cost savings in the paper-making process are introduced due to the dual function of the biocide.

As a result of being able to use the biocidal emulsifying agent as an internal paper size emulsifier, the final paper product is made stronger and more durable. Strength is achieved by improving resistance to fluids through effective sizing. Durability is achieved by improving resistance to microorganisms.

Compared to prior art internal paper size emulsions utilizing emulsifying agents that combine a starch, a polymer and a surfactant, the claimed biocidal sizing emulsion contributes to improving the efficiency of the paper-making process. This is due to the fact that one compound, the biocide, is taking the place of several chemical additives. No starch, polymer or surfactant is required, yet the sized paper made with the biocidal sizing emulsion also has the beneficial property of being resistant to growth of microorganisms without addition of an additive that is separate from the size emulsifying agent.

Also, when a non-starchy, cationic quaternary ammonium compound is selected as the biocidal emulsifying agent, an additional surprising improvement in the paper-making process efficiency is realized. Foam, which is usually associated with utilizing quaternary ammonium compounds in a paper furnish, is reduced or is severely destabilized. Neither an anti-foaming nor a de-foaming agent is required to control the foam. Thus, efficiency associated with utilizing one compound to accomplish three functions previously known to require at least three separate compounds, is attributed to the biocidal emulsifying agent used in the biocidal sizing emulsion.

The biocidal emulsifying agent used in the biocidal sizing emulsion is cationic, providing good retention in the paper sheet, reducing the need for complicated wet-end retention chemistry. Dry end quality control testing for adequate and consistent biocide dosing is also minimized. These improvements in the paper-making process are expected to result in less complex, less expensive and more consistent procedures and results of manufacturing of paper facers and the gypsum panels that the paper facers cover.

An ASA emulsion utilizing the biocidal emulsifying agent remains stable longer, improving manufacturing efficiency and workability of the ASA paper size. It is contemplated that a biocidal sizing emulsion made with AKD can also be made at a paper-mill or a gypsum manufacturing plant, thereby reducing the expense of transporting pre-emulsified AKD and the large quantity of water associated with it.

Another important feature of this invention is that a biocidal gypsum panel can be made without resorting to fiberglass or other less-desirable, non-paper facers. It is also an improvement to provide for more biocide in the paper cover sheet, which is a paper ply closer to the surface of the gypsum panel, where most of the mold, mildew, or fungus defacement problem is most likely to accrue.

DETAILED DESCRIPTION

The present invention provides a biocidal sizing emulsion where one phase is an internal paper sizing agent and a biocidal emulsifying agent. The second, continuous phase is water. No other biocide or emulsifying agent need be present in the biocidal sizing emulsion of this invention. The biocidal sizing emulsion may be utilized in manufacturing of paper facers for gypsum boards. The biocidal sizing emulsion provides an improved method of manufacture that is more efficient and commercially viable, as well as an improved product with the biocidal emulsifying agent that is better retained in a product, such as a paper facer.

Compounds referred to herein as "biocidal emulsifying agents" are limited to biocides which emulsify internal paper size and become part of the finished paper product so that anti-microbial properties are imparted to the paper product. A biocidal additive ("biocide") to paper is effective in reducing microorganism growth on wallboard panels and their facers. The terms microbe, bacteria, mold, mildew and fungus are used interchangeably to refer to the many microorganisms that could potentially grow on these surfaces.

Preferred internal sizing agents are alkenyl succinic anhydride ("ASA") and alkyl ketene dimmer ("AKD"). The ASA internal size is an oily liquid at room temperature. It is stored where it can remain dry, as it is very unstable. It will react with water or water vapor to hydrolyze and become unusable as an internal sizing agent. An example of the ASA size that is effective in this invention is Bubond 650. (Buckman Laboratories, Memphis, Tenn.). Also, Prequel® 1000/Prequel@ 630 (Ashland Hercules, Wilmington, Del.) and Nalco® 7548/Nalco® 7540 (Nalco, Naperville, Ill.) are additional examples of the ASA size.

In one embodiment, a biocidal sizing emulsion of the internal paper size is made with the biocidal emulsifying agent and water. Preferably, ASA internal paper size is emulsified with a biocidal emulsifying agent that is a non-starchy cationic quaternary ammonium compound. More specifically, quaternary ammonium compounds useful in this biocidal sizing emulsion are alkyl dimethyl benzyl ammonium chloride (ADBAC), alkyl dimethyl ethyl benzyl ammonium chloride (EBC), dialkyl dimethyl ammonium chloride, didecyl dimethyl ammonium chloride, and combinations thereof. In another embodiment, the non-starchy cationic biocide is one or a combination of dequalinium chloride, didecyl-dimethylphosphonium chloride, didodecyl-ethyl-isobutylphosphonium, a dihexyldecyl-ethyl-isobutylphosphonium, a long chain alkyl amine, a guanidine, a bis (3-aminopropyl) dodecylamine, polyaminopropyl biguanide or iodopropynyl butylcarbamate. When one of these biocidal emulsifying agents is selected to emulsify the internal paper size, no additional emulsifying agent is required. Polymers, surfactants, starches, and other compounds known to emulsify or stabilize ASA and AKD can be eliminated.

Emulsification of the internal size provides small droplets to allow for efficient anchoring of the size to the paper pulp fibers. The ASA size is a hydrophobic, oily liquid that is typically 100% solids. The biocidal emulsifying agent is typically 20% to 80% solids and is first diluted with primary water in a static mixer. The amount of the primary water used for dilution of the biocidal emulsifying agent is approximately 10% of the total emulsification process water requirement for a 40% solids biocide. Little or no water may be required when a biocidal emulsifying agent is lower in solids than 40%. A stream of diluted biocidal emulsifying agent is combined with a stream of 100% solids ASA, and the resultant solution is pumped through a turbine pump at a differential pressure between 200-230 psi to make a biocidal sizing emulsion. Droplets in the biocidal sizing emulsion range in size from 0.5 microns to 1.5 microns in diameter. The stream of the biocidal sizing emulsion is further diluted with secondary water. The solids of the emulsified ASA can be adjusted to a concentration of approximately 1% and pumped into a paper-making furnish. Depending on operating conditions, the final solids concentration of the emulsified ASA may be adjusted lower or higher than 1%; but once the emulsification dilution water is determined for a particular paper machine it need not be adjusted.

The amount of biocidal emulsifying agent utilized in the biocidal sizing emulsion is directly related to the amount of biocide needed to control microorganism growth and the amount needed to emulsify the size. Papers with different compositions are made for application in different environments, thus the antimicrobial requirement can increase or decrease depending on the likelihood that there will be sufficient nutrition, moisture and other factors that promote growth of microorganisms. Likewise, the size may call for different amounts of emulsifying agent depending on the quantity of size required to achieve sufficient protection from fluids for the paper being made. This acceptable dosage or concentration of biocidal emulsifying agent will then be used to emulsify the ASA and checked for particle size, foaming and emulsion stability.

A size dosage is determined by evaluating the water resistance needed to produce the grade or type of paper. Generally, these grades are higher in water resistance because both mold and water resistance is required for these grades. The ratio of the internal size, also known as a sizing agent, to the biocidal emulsifying agent is preferably one part size to one part biocidal emulsifying agent. The ratio may range from 1:1 to 1:0.5 size to biocidal emulsifying agent. The quantity of size varies, but is generally between 2 lb/ton to 20 lb/ton of air dried paper; or more typically between 5 lb/ton to 10 lb/ton. For example, a 5000 ppm ASA emulsified size will contain 41.2% biocide emulsifying agent, or 2060 ppm, and the remaining material is ASA size.

In Example 2, below, a method of selecting a concentration of biocidal emulsifying agent is demonstrated. For example, the 2060 ppm of biocidal emulsifying agent described above must show no mold growth after treating a standard 1% CMC solution with 0.25% ASA size mixture.

It is contemplated that the AKD internal size would be an alternative and workable substitute for the ASA in the biocidal sizing emulsion of this invention. The AKD biocidal sizing emulsions could be made at the paper-mill or gypsum panel manufacturing plan thereby reducing the expense of transporting the pre-emulsified AKD and the large quantity of water associated with it. Further, it is contemplated that a surfactant or polymer may be utilized with the biocidal sizing emulsion of the present invention. One embodiment includes utilization of a non-anionic surfactant or polymer in the biocidal sizing emulsion.

Emulsifying an ASA or AKD sizing agent with a biocidal emulsifying agent is accomplished by utilizing known emulsification methods. No changes to standard equipment are required, but small changes in flow rates or turbine back pressures may occur to produce the biocidal sizing emulsion of suitable quality, i.e. particle size, distribution and stability.

An exemplary method utilized for emulsifying ASA size in the laboratory is described. First, tare a Senco mini blender cup and add 1 gram of ASA size to the cup. Then add 0.7 grams of the biocidal emulsifying agent to the cup with the ASA size and add enough water to make a 100 gram biocidal sizing emulsion with the above two ingredients. Place the Senco cup on a blender and turn the blender on high for 90 seconds. A 100 gram quantity of ASA size is ready to treat a dilute suspension of paper fibers. If needed, the emulsifier ratio can be adjusted depending on solids and the quality of the emulsion.

In another embodiment, a sized multi-ply paper is produced. There are optionally two emulsifying units to minimize any paper manufacturing equipment down time. One or more paper plies are made with the biocidal emulsifying agent and size blend to prevent mold and a second emulsifying agent may be used to produce a sized paper under normal emulsification procedures. This reduces the sizing cost and allows the biocide to treat just the outer paper plies which are exposed to mold spores. The biocidal sizing emulsion is optionally added to the paper furnish by adding it to the suction side of a fan pump, but could be added on the pump pressure side.

Selection of the biocidal emulsifying agent for the paper making process utilizes the same criteria that applies to selection of the biocidal emulsifying agent for the biocidal sizing emulsion. There is a balance of how much water to add and final dilution in the paper machine. As more water is added, the size is better dispersed and it becomes more uniformly distributed. However, additional water adds additional expense because the water is typically softened. This may change the water balance of the paper making process, causing the plant to discharge some process water.

The biocidal sizing emulsion at 1% solids is stored in a small tank that will turnover every 30 to 60 minutes to minimize hydrolysis. The size is pumped to the fan pump using a centrifuge at low pressure, 20 to 25 psi. Adding the sizing solution to a paper furnish by measuring the consistency, flow rate of the fibers and the percent solids, as well as the flow rate of the dilute size., the paper-making process can be completed on any conventional paper-making machine. Often, paper facers are made with several plies or layers. Sometimes, as few as two plies are used. Other times, as many as seven or more plies are utilized. Paper additives or size may be added to the paper furnish through a head box or before a refiner, but are normally added to the fan pump that feeds the dilute furnish to a headbox.

Yet another embodiment of this invention utilizes the above-described emulsion and paper in a method of making a mold-resistant gypsum panel that includes selecting the biocidal emulsifying agent, emulsifying the ASA or AKD internal sizing agent with the biocidal emulsifying agent to form the biocidal sizing emulsion, adding the biocidal sizing emulsion to the paper furnish that will be processed to form the paper facer upon which a gypsum slurry will be placed and set to form a gypsum panel or board. Paper facers are often manufactured by gypsum board manufacturers as part of the gypsum board manufacturing process.

Preparing a slurry of calcium sulfate hemihydrate and water is made according to conventional gypsum slurry methods. Calcium sulfate hemihydrate and water in excess of the amount needed to rehydrate the calcium sulfate hemihydrate are mixed to form a flowable slurry. Additives such as starch, foam, accelerator, dispersing agent, etc. are contemplated as part of the gypsum slurry. There are no adverse or desirable interactions between the additives and the biocidal paper facer.

The antimicrobial paper facer that is made with the furnish enhanced by the biocidal sizing emulsion is made to roll along a forming table on a conveyor belt. The gypsum slurry is continuously deposited onto the facer. As the paper and slurry traverse the conveyor, a second paper facer may be placed onto the top surface of the gypsum slurry before it sets. Setting of gypsum slurry involves an exothermic reaction whereby water is taken up by the calcium sulfate hemihydrate and gypsum crystals are formed. As more and more crystallization takes place, the slurry becomes more and more solid. Setting progress is measured by the rise in temperature of the slurry. In a gypsum board manufacturing plant, it is useful to take the temperature of the material on the conveyor at the point where it is to be cut by a knife into the desired size board pieces. The finished gypsum board is microbe-resistant as a result of having at least one antimicrobial paper facing. It is contemplated that a biocidal emulsifying agent may be added to the gypsum slurry, and therefore be present in the gypsum core as well.

The following examples are meant to further explain and illustrate the invention. The Examples are not intended to limit the scope of the invention.

EXAMPLE 1

Laboratory paper handsheets were produced with various internal size emulsions. The sheets showed excellent resistance to water absorption, as well as good resistance to microorganism growth. Size emulsions for the paper sheets were made with NALCO® 7540 ASA size, manufactured in Naperville, Ill. The size was combined with each of the antimicrobial components in Tables I and II in a 10:1 weight ratio of ASA size to biocidal emulsifying agent.

The biocidal emulsifying agents were quaternary ammonium chloride compounds that were obtained from Mason Chemical Company in Joliet, Ill. MAQUAT® MC1416 and MAQUAT® MC1412 were both 80% active alkyl dimethyl benzyl ammonium chloride (ADBAC) compounds. MAQUAT® MQ2525 was an 80% active combination of alkyl dimethyl benzyl ammonium chloride and alkyl dimethyl ethyl benzyl ammonium chloride. MAQUAT® MQ624M was received as an 80% active biocidal emulsifying agent, but was diluted and utilized in the laboratory as a 45% active combination of alkyl dimethyl benzyl ammonium chloride and dialkyl dimethyl ammonium chloride.

MAQUAT® 4480E, didecyl dimethyl ammonium chloride, was similarly diluted from 80% to 45% biocidally active compound.

Four gram, two-ply hand sheets were made in a laboratory procedure that utilized a British laboratory hand sheet mold. 100% old corrugated container ("OCC") furnish was pulverized to make a fibrous pulp. Biocidal sizing emulsions of ASA in the various biocides shown in Table I were made by adding an aqueous solution of the biocidal emulsifying agent with the size, according to the Laboratory Method of Emulsifying ASA Size set forth above, to achieve properly sized droplets of emulsified ASA. This aqueous biocidal sizing emulsion was further diluted with additional water to obtain a 1% or low dilution of ASA size and biocidal emulsifying agent. The paper furnish slurry of pulp, water and emulsified size was then pressed in an Adirondack roll press at 20 psi and the resultant sheets were dried in a laboratory drum dryer at 240° F. for 2.5 minutes.

These hand sheets were then tested for water and mold resistance. The water resistance tests included a TAPPI T441 Standard Cobb Test, herein incorporated by reference, and a Boiling Boat Test, which measures how long (up to 1,000 seconds) it takes for boiling water to soak through 50% of the paper sheet. The Cobb Test was operated at 120° F. for 3 minutes.

The Boiling Boat Test included floating a piece of paper on boiling water to determine the degree of water repellency. Paper samples were prepared by cutting 12"×12" pieces of paper to be tested. The paper sample was placed bond-side (bond-side is the side that is attached to the gypsum panel) down on a flat surface. A 6"×6" jig, or a solid, flat object, was placed directly in the center of the piece of paper. With the jig as an aid, creases along each edge of the jig and across the corners were made to form a three-dimensional boat-like structure out of the piece of paper. One corner of the paper sample was folded up and over to an adjacent side, then stapled in place. Two staples in each corner worked well. This folding and stapling was repeated for each side to make the boat and hold the paper in the boat formation. A 4'×4' rubber stamp was used to make an impression of a grid in the center (or as close as possible to the center) of the bottom of the paper boat.

An aluminum or stainless steel tray, measuring 10" square and 3" deep, was placed on a hot plate that was at least 10" square. The tray was filled approximately ⅔ full of water, a thermometer was put into the water, and the hot plate heat was turned to "high." When the water reached 97° C.±3° C., the paper boat was placed into the water while starting a stopwatch. When the paper or a portion of the paper became wet it was observable as a darkening of the wet area. The measurable area in the grid on the bottom of the boat that was darkened was measured after 5 and 15 minutes, provided the paper did not reach 50% wetted. The test was stopped when 50% (12-13 squares of the grid) was wetted or after 15 minutes (1,000 seconds).

To measure the wetness of the bottom of the boat, the number of grid squares that were wetted through was counted. Estimates to the nearest ¼ square were made. The number of squares was multiplied by 4 to determine the percent of wetting.

Table I shows Cobb and Boiling Boat test results for size efficacy of ASA size in various biocidal sizing emulsions. Both sets of test results indicate very good sizing of the paper. No polymer was included in these samples, labeled with letter and number codes from B1 to F3. Sample A was a control with no biocidal emulsifying agent and only ASA internal size and a polymer (NALCO® 7541) emulsifying agent.

Table II shows Cobb and Boiling Boat test results for size efficacy of ASA size in NALCO® 7541 polymer emulsions. Comparison of the Cobb and Boiling Boat test results shows very good sizing in all samples. This conclusion was supported by the fact that it took more than 1,000 seconds (17 minutes) to wet 50% of the paper in the Boiling Boat Test. The Cobb Test results were also very good. It was surprising that ASA internal size was just as effective when emulsified with a biocidal emulsifying agent as it was when emulsified, according to standard practice, with a polymer.

TABLE I

| Code | Biocide | Size #/ton | Polymer #/ton | Biocide #/ton | Cobb g/100 cm$^2$ | Boiling Boat seconds |
| --- | --- | --- | --- | --- | --- | --- |
| A | Control (none) | 10 | 7 | 0 | 0.49 | 1000+ |
| B1 | MAQUAT MC 1416 | 10 | 0 | 1 | 0.51 | 1000+ |
| B2 | MAQUAT MC 1416 | 20 | 0 | 2 | 0.56 | 1000+ |
| B3 | MAQUAT MC 1416 | 30 | 0 | 3 | 0.48 | 1000+ |
| C1 | MAQUAT MC1412 | 10 | 0 | 1 | 0.49 | 1000+ |
| C2 | MAQUAT MC1412 | 20 | 0 | 2 | 0.52 | 1000+ |
| C3 | MAQUAT MC1412 | 30 | 0 | 3 | 0.51 | 1000+ |
| D1 | MAQUAT MQ2525 | 10 | 0 | 1 | 0.54 | 1000+ |
| D2 | MAQUAT MQ2525 | 20 | 0 | 2 | 0.53 | 1000+ |
| D3 | MAQUAT MQ2525 | 30 | 0 | 3 | 0.49 | 1000+ |
| E1 | MAQUAT MQ624M (modified) | 10 | 0 | 1 | 0.65 | 1000+ |
| E2 | MAQUAT MQ624M (modified) | 20 | 0 | 2 | 0.58 | 1000+ |
| E3 | MAQUAT MQ624M (modified) | 30 | 0 | 3 | 0.55 | 1000+ |
| F1 | MAQUAT 4480E | 10 | 0 | 1 | 0.63 | 1000+ |
| F2 | MAQUAT 4480E | 20 | 0 | 2 | 0.66 | 1000+ |
| F3 | MAQUAT 4480E | 30 | 0 | 3 | 0.57 | 1000+ |

TABLE II

| Code | Biocide | Size #/ton | Polymer #/ton | Biocide #/ton | Cobb g/100 cm$^2$ | Boiling Boat seconds |
|---|---|---|---|---|---|---|
| G1 | FUNGITROL 920-20% | 10 | 7 | 1 | 0.62 | 1000+ |
| G2 | FUNGITROL 920-20% | 20 | 7 | 2 | 0.58 | 1000+ |
| G3 | FUNGITROL 920-20% | 30 | 7 | 3 | 0.60 | 1000+ |
| H1 | FUNGITROL 11-100% | 10 | 7 | 1 | 0.57 | 1000+ |
| H2 | FUNGITROL 11-100% | 20 | 7 | 2 | 0.62 | 1000+ |
| H3 | FUNGITROL 11-100% | 30 | 7 | 3 | 0.63 | 1000+ |

All samples, A-H3, shown in Tables I and II, plus another control were also subjected to a modified ASTM G21 Fungal Defacement Test. The control ensured that the test would grow mold and the sizing performance would be similar to the control. Two, one square inch, paper samples were cut form each handsheet and were placed on solidified nutrient-salt agars in a Petri dish so each paper side was tested. The Petri with paper samples dish were incubated at 28-30° C. with a relative humidity greater than 85% for a period of time before it was observed. The paper samples were wetted with sterile water and contain only the mold spores from the air.

At 7 and 14 days the front and the back of the paper sheet samples were inspected for surface microbial growth. The results are shown in Table IV. A value of "0" indicates no microbial growth on the sample surface. A value of "1" indicates 1-10% growth; "2" indicates 11-30% growth; "3" indicates 31-60% growth; and "4" indicates greater than 61% growth. The ratings of the paper samples in Table IV are shown in Table III as follows:

TABLE III

| Minimum Time Frame | Growth | Maximum Time Frame | Growth | ASTM G-21 USG Rating | General Rating |
|---|---|---|---|---|---|
| Less than 7 days | Shows growth | 7 days | Shows growth | 3 to 4 | Not fungus resistant |
| 7 days | No growth | 14 days | Shows growth | 3 to 4 | Not fungus resistant |
| 7 days | No growth | 14 days | Sparse growth | 0 to 2 | Moderately fungus resistant |
| 7 days | none | 14 days | None | 0 | Fungus resistant |

TABLE IV

| SAMPLE CODE | 7 DAYS Front | 7 DAYS Back | 14 DAYS Front | 14 DAYS Back |
|---|---|---|---|---|
| A | 0 | 4 | 4 | 4 |
| B1 | 1 | 3 | 4 | 4 |
| B2 | 1 | 0 | 2 | 1 |
| B3 | 2 | 1 | 4 | 4 |
| C1 | 4 | 4 | 4 | 4 |
| C2 | 1 | 4 | 4 | 4 |
| C3 | 2 | 1 | 4 | 4 |
| D1 | 1 | 4 | 4 | 4 |
| D2 | 1 | 0 | 4 | 1 |
| D3 | 4 | 4 | 4 | 4 |
| E1 | 2 | 0 | 4 | 4 |
| E2 | 0 | 1 | 4 | 4 |
| E3 | 4 | 4 | 4 | 4 |
| F1 | 0 | 2 | 4 | 4 |
| F2 | 4 | 4 | 4 | 4 |
| F3 | 4 | 4 | 4 | 4 |
| CONTROL | 4 | 4 | 4 | 4 |

The sample codes in Table IV refer to the same sample codes in Tables I and II. Sample A was a control. Biocidal effect is observed in samples with biocidal emulsifying agent added. It is contemplated that increasing the concentration of biocidal emulsifying agent will improve the antimicrobial performance of the paper.

EXAMPLE 2

The biocidal size emulsion was utilized in a method of making a mold-resistant paper facer that included selecting a biocidal emulsifying agent. One method of selecting a concentration of a singular or a blend of several biocidal emulsifying agents was to complete a series of dilutions of the components prior to emulsifying the ASA or treating the paper. A medium to low molecular weight carboxyl methyl cellulose ("CMC"), an emulsion stabilizer, at 1% and 0.25% ASA size was blended in a beaker as a standard solution. Five milliliters of this standard solution was pipetted into eight different sterile test tubes. The test biocidal emulsifying agent was diluted to make a 2.5% solution. See Table V.

TABLE V

| Test Tube | Biocide Conc (ppm) | CMC + ASA Size (ml) | Sterile Water (ml) | Spores 10,000 cfu | Biocide 2.5% | Total (ml) |
|---|---|---|---|---|---|---|
| 1 | 0 | 5.0 | 4.8 | 0.2 | 0 | 10 |
| 2 | 10,000 | 5.0 | 0.8 | 0.2 | 4.0 | 10 |
| 3 | 5,000 | 5.0 | 2.8 | 0.2 | 2.0 | 10 |
| 4 | 2,500 | 5.0 | 3.8 | 0.2 | 1.0 | 10 |
| 5 | 1,250 | 5.0 | 4.3 | 0.2 | 0.5 | 10 |
| 6 | 625 | 5.0 | 4.55 | 0.2 | 0.25 | 10 |
| 7 | 312 | 5.0 | 4.67 | 0.2 | 0.13 | 10 |
| 8 | 156 | 5.0 | 4.74 | 0.2 | 0.06 | 10 |

A 1 ml aliquot was placed in a petri dish and observed after 3, 5 or 7 days. The mold colonies were counted on each Petri dish to obtain no fungal colonies at the lowest biocidal emulsifying agent concentration. After these tests were completed a standard handsheet was made using the biocide to emulsify the ASA size. Sizing performance was evaluated, paper properties were measured and ASTM G21 fungal testing was completed on the paper.

It is contemplated that greater quantities of biocidal emulsifying agent would improve the microorganism resistance without compromising the sizing or other properties of the paper product.

While particular embodiments of the biocidal size emulsification, the biocidal paper facer and the biocidal gypsum panel have been shown and described, it will be appreciated by those skilled in the art that changes and modifications may be made thereto without departing from the invention in its broader aspects and as set forth in the following claims.

What is claimed is:

1. A mold-resistant gypsum panel comprising:
a gypsum core;
at least one facer comprising
paper made from a furnish that includes a paper sizing emulsion comprising an emulsion of a biocidal emulsifying agent and an internal sizing agent, wherein the biocidal emulsifying agent is a non-starchy quaternary ammonium compound, and wherein the internal sizing agent and biocidal emulsifying agent are emulsified in water.

2. The mold-resistant gypsum panel of claim 1 wherein said emulsion is free of additional emulsifying agents.

3. The mold-resistant gypsum panel of claim 1 wherein said internal sizing agent is selected from the group consisting of alkenyl succinic anhydride and alkyl ketene dimer.

4. The mold-resistant gypsum panel of claim 1 wherein said internal sizing agent is alkenyl succinic anhydride.

5. The mold-resistant gypsum panel of claim 1 wherein the biocidal emulsifying agent is a non-starchy cationic quaternary ammonium compound.

6. The mold-resistant gypsum panel of claim 1, wherein said non-starchy quaternary ammonium compound is at least one selected from the group consisting of alkyl dimethyl benzyl ammonium chloride, alkyl dimethyl ethyl benzyl ammonium chloride, dialkyl dimethyl ammonium chloride, didecyl dimethyl ammonium chloride, and combinations thereof.

7. The mold-resistant gypsum panel of claim 1, wherein said biocidal emulsifying agent is selected from the group consisting of dequalinium chloride, didecyl-dimethylphosphonium chloride, didodecyl-ethyl-isobutylphosphonium, dihexyldecyl-ethyl-isobutylphosphonium, long chain alkyl amines, guanidines, bis (3-aminopropyl) dodecylamine and polyaminopropyl biguanide, or a combination thereof.

8. The mold-resistant gypsum panel of claim 1, wherein the ratio of the internal sizing agent to the biocidal emulsifying agent is 1.5 parts of the internal sizing agent to one part of the biocidal emulsifying agent.

* * * * *